United States Patent [19]

Budinger

[11] Patent Number: 4,926,703
[45] Date of Patent: May 22, 1990

[54] METHOD AND APPARATUS FOR DETERMINATION AND DISPLAY OF CRITICAL GAS SUPPLY INFORMATION

[76] Inventor: William D. Budinger, 16 Southridge Dr., Kennett Square, Pa. 19348

[21] Appl. No.: 308,509

[22] Filed: Feb. 9, 1989

Related U.S. Application Data

[60] Division of Ser. No. 169,651, Mar. 21, 1988, Pat. No. 4,876,903, which is a continuation-in-part of Ser. No. 142,370, Jan. 11, 1988, abandoned.

[51] Int. Cl.$^5$ ............................................. G06F 15/42
[52] U.S. Cl. .................................................. 73/865.1
[58] Field of Search ............... 73/865.1, 714; 364/418, 364/705, 413.3, 413.31; 128/205.23; 340/700, 717

[56] References Cited

U.S. PATENT DOCUMENTS

| | | |
|---|---|---|
| 3,364,476 | 1/1968 | Kahn . |
| 4,109,140 | 8/1978 | Etra . |
| 4,586,136 | 4/1986 | Lewis . |
| 4,658,358 | 4/1987 | Leach . |
| 4,753,117 | 6/1988 | Osterhout et al. . |
| 4,782,338 | 11/1988 | Barshinger . |
| 4,809,550 | 3/1989 | Faulconer .......................... 73/865.1 |

*Primary Examiner*—Robert R. Raevis
*Attorney, Agent, or Firm*—Panitch, Schwarze, Jacobs & Nadel

[57] ABSTRACT

An apparatus for and method of determining and displaying important information pertaining to the use of breathable bottled gas in a pressurized fixed volume container. The apparatus determines and displays information such as consumption rate, gas requirement for future activity, gas time remaining under present and future conditions, as well as other information about the environment in a form that clearly shows critical parameters in an easily understood and intuitive Pictorial Display. The apparatus comprises transducers for measuring ambient pressures and the pressures of the bottled gas, processors or microprocessors for interpreting and analyzing the data and making the necessary computations, and a display screen for presenting information to the user.

3 Claims, 3 Drawing Sheets

METHOD AND APPARATUS FOR DETERMINATION AND DISPLAY OF CRITICAL GAS SUPPLY INFORMATION

CROSS REFERENCE TO RELATED APPLICATION

This is a division of application Ser. No. 169,651, filed Mar. 21, 1989, now U.S. Pat. No. 4,876,903, which is a continuation-in-part of Ser. No. 142,370, filed Jan. 11, 1988, (now abandoned) and entitled, "Determination and Display of Remaining Gas Supply Times."

FIELD OF THE INVENTION

This invention relates to systems for breathing a breathable gas from a pressurized fixed-volume container such as SCUBA, medical and aircraft oxygen, and the like, and, in particular, relates to the determination and display of important information such as the gas consumption rate, the gas required for future activity, the gas time remaining under present and future conditions, and the like, in a form that clearly shows the information in an easily understood and intuitive pictorial display.

BACKGROUND OF THE INVENTION

In the use of self-contained or supplemental breathing systems which draw from a fixed volume source, it is often desirable for the user to be able to predict how long the remaining air or gas supply will last. In SCUBA (Self Contained Underwater Breathing Apparatus) diving, for example, it is particularly useful to know how long a diver may continue at his present task and still have enough air to make a safe ascent to the surface. For systems supplying oxygen gas to people in unpressurized aircraft, it is useful to know how long the supply of oxygen will last, particularly if the aircraft changes altitude.

Present practice makes use of pressure gauges to tell the user how much air or gas pressure he has left, and charts which list schedules showing how much time can be expected for a given tank volume and pressure. In SCUBA diving, for example, divers are trained to know that a typical 72 cubic foot tank pressurized to 2250 psi will last about 1 hour at a depth of 33 feet (10 meters). The diver also knows that that same amount of air will last him only half as long at a depth of 99 feet (30 meters). Clearly, estimating how much time remains on a given supply of air is exceedingly difficult for a diver changing depths or an aviator changing altitudes.

The reason that endurance time varies with depth or altitude is due to a combination of human physiology and Boyle's Law of gases. A typical person can inhale and exhale about 4 liters of air with one breath. This breath volume stays the same whether he is in an unpressurized airplane at 18,000 feet or in a pressurized diving bell 200 feet below the surface of the sea. However, the actual amount of gas represented by each breath at these two extremes is very different. According to Boyle's Law, for any given volume, the number of gas molecules is directly proportional to the absolute pressure (all other things being unchanged). At 18,000 feet, the absolute pressure is about one half an atmosphere (½ Bar). At a depth of 200 feet of sea water, the absolute pressure is about 7 atmospheres (7 Bars). This means that a person breathing 4 liter breaths at a depth of 200 feet is using about 14 times as much air per breath as a person at 18,000 feet. If the person is breathing from a fixed supply such as a tank, ambient pressure has a tremendous effect on how long that tank will last. For example, a 72 cubic foot SCUBA tank will provide air for about 3 hours to an aviator at 18,000 feet altitude and about 13 minutes to a diver 200 feet under the surface of the sea.

In the following discussion, the term "air" is used for simplicity, but "air" should be taken to mean any breathable gas or mixture of breathable gasses. Air supply levels and consumption rates are referred to in terms of pressure rather than volume or mass because pressure and pressure changes are easy to measure and work well for the present purpose. To illustrate the invention, the SCUBA model will be used although the principles apply equally to other situations where gas is being breathed from a fixed volume container.

Estimating the amount of time a SCUBA diver's compressed air supply will last is exceedingly important. As might be expected, such estimates are very difficult to make accurately when the diver operates at many different depths. Further, the diver must leave the depths before his air runs out; he must have enough air left in his tanks to make the surface safely.

The prior art has attempted to estimate remaining gas consumption time in various ways. The most common method has been to measure the gradual reduction in gas supply pressure and then to calculate remaining time by extrapolating that reduction rate over the remaining gas supply pressure. Another method has been to estimate a breathing consumption rate at the surface and then adjust that rate for ambient diving pressure to estimate gas consumption during the dive. Both methods ignore the gas required for ascent and so have no way of providing the diver with accurate information about how much longer he can safely stay without running out of gas on his ascent. Also, both methods mislead the diver because they make no allowance in their projections for the fact that the diver's consumption rate will change when he changes depth, as the diver must do when he ascends to the surface, or the fact that the consumption rate measurements may have been made unreliable by significant non-breathing events.

The prior art approach does not take into account other potential causes for changes in tank air pressure. Temperature, for example, can have as large an effect on tank air pressure as breathing consumption. For example, when a SCUBA diver descends from the warm surface to the cold depths, he may see a water temperature change of 15 degrees centigrade or more. For a tank pressurized to 3000 psi, the drop in pressure caused by the chilling could be greater than the drop caused by 5 minutes of breathing. Clearly, any estimate and projection of breathing consumption would be very misleading. Also, a diver occasionally uses air for non-breathing purposes such as clearing his regulator, inflating his buoyancy compensator, or inflating a lift bag. Obviously, it is desirable for a device that is to make accurate calculations of consumption not to be fooled by factors other than breathing.

It would be very desirable if the diver had a way to estimate how long his remaining air supply will last in various situations. In particular, it would be useful for a diver to know if he has time to finish his present task before his diminishing air supply will require surfacing. If the diver must undergo a decompression regimen, the amount of air required for ascent can represent a substantial portion of the total air supply he has available for the dive. An accurate estimate of the air required for decompression can be extremely important to the safety of the dive.

Conventional means for displaying information to the diver is in the form of numbers or simple bar graphs. As the amount of information required to be displayed becomes greater, the opportunities for the diver to become confused increase dramatically. This problem is aggravated at depth by nitrogen narcosis. Narcosis, caused by the combined effects on the human brain of nitrogen and pressure, resembles intoxication. Narcosis greatly increases the difficulty of understanding displays which would be simply understood on the surface.

For the purposes of this patent, the terms below have the following meanings. Where the word "air" is used, it should be taken to mean any breathable gas.

Ceiling—In dives requiring decompression, the ceiling is the shallowest underwater depth to which a diver may ascend without risking decompression sickness. During decompression, the ceiling slowly rises, finally reaching the actual water surface and allowing the diver to safely leave the water.

DCS—Decompression sickness (bends) results from formation of gas bubbles (usually nitrogen) in body tissues. Gas absorbed by tissues when a diver is breathing pressurized air at depths greater than about 20 feet can accumulate to a point where it will create bubbles and cause DCS if the diver ascends too quickly.

Decompression—A required delay or series of delays during a diver's ascent to allow dissolved gas in the tissues time to dissipate without the formation of bubbles and thus prevent DCS. The term may also refer to a dive that will require the diver to make decompression stops instead of ascending directly to the surface.

Remaining Air Time (RAT)—The amount of time a fixed volume of gas would last at the present gas consumption rate and the present ambient pressure.

Adjusted Remaining Air Time (ARAT)—The amount of time a fixed volume of gas would last at the present gas consumption rate (RAT) if the rate were modified according to Boyle's Law for ambient pressures other than the pressure at which the gas consumption rate was originally determined.

No-Decompression Time (NDT)—The amount of time a diver may remain at a particular depth without being required to decompress when he ascends to the surface.

No-Decompression Line (ND)—On a graph of time and depth, a curve that represents the limits to which a diver may go without being required to decompress.

Safe Ascent Profile (SAP)—A schedule of depths and times representing a diver's optimum safe route to the surface, including any stops required for Decompression or any delays needed to allow the Ceiling to reach the surface. When calculated from Ceiling information, the SAP normally projects the diver to ascend to some predetermined depth below the Ceiling (such as 5 feet) and remain below the Ceiling until the Ceiling reaches the surface.

Ascent Air Requirement (AAR)—The amount of air that will be required for a diver's safe ascent to the surface, including air required for any delays needed for decompression. This value may also be referred to as the air required for decompression.

Safe Air Limit (SAL)—The point in time in the future where the air consumed at the present air consumption rate plus the Ascent Air Requirement (AAR) will just equal the remaining available air supply, less any allowances for reserve. The SAL may be adjusted to give an SAL for depths other than the present.

Safe Operating Envelope (SOE)—On a two-dimensional graph of time and depth, that area of the graph representing the times and depths where a diver may operate safely. In a dive where decompression is not permitted, the SOE is normally bounded by the ND line and the surface (if air supply is not considered). Where decompression is required, the SOE is normally bounded by the SAL line and the ceiling.

Event Window—In the selection of qualifying breathing events, an Event Window defines the maximum and minimum pressure drops within which an event is considered to be a qualifying event.

Pictorial Display—A means of presenting complex information in a simple form by using a two dimensional chart or graph with axes chosen so that the user's condition can be easily viewed in spatial relationship to other conditions or options.

SUMMARY OF THE INVENTION

In one aspect, the invention is a method of accurately determining breathing gas consumption rate in an environment where factors other than breathing are influencing the consumption rate signal.

In another aspect, the invention is a method of determining and displaying the Remaining Air Time at the present consumption rate and at the present depth or ambient pressure and then adjusting and displaying the effect on RAT of projected changes in depth or ambient pressure.

Still another aspect provides a means of determining how much longer a SCUBA diver may remain at his present or other depths and still have enough breathable gas to get to the surface safely.

A further aspect provides a means of displaying critical safety information or information concerning the amount of breathable gas or the consumption time remaining to the user in a Pictorial manner that allows simple intuitive understanding of the user's safe options.

The invention further includes an apparatus, preferably incorporating a microprocessor, adapted to perform the steps of the aforesaid aspects and incorporated in a portable, battery powered instrument small enough to be easily carried by a user.

BRIEF DESCRIPTION OF THE DRAWINGS

The foregoing summary, as well as the following detailed description of the invention will be better understood when read in conjunction with the appended drawings. For the purpose of illustrating the invention, there is shown in the drawings embodiments which are presently preferred. It is understood, however, that the invention is not limited to the precise arrangements and instrumentalities shown. In the drawings.

DETAILED DESCRIPTION OF THE INVENTION

Figure 1:
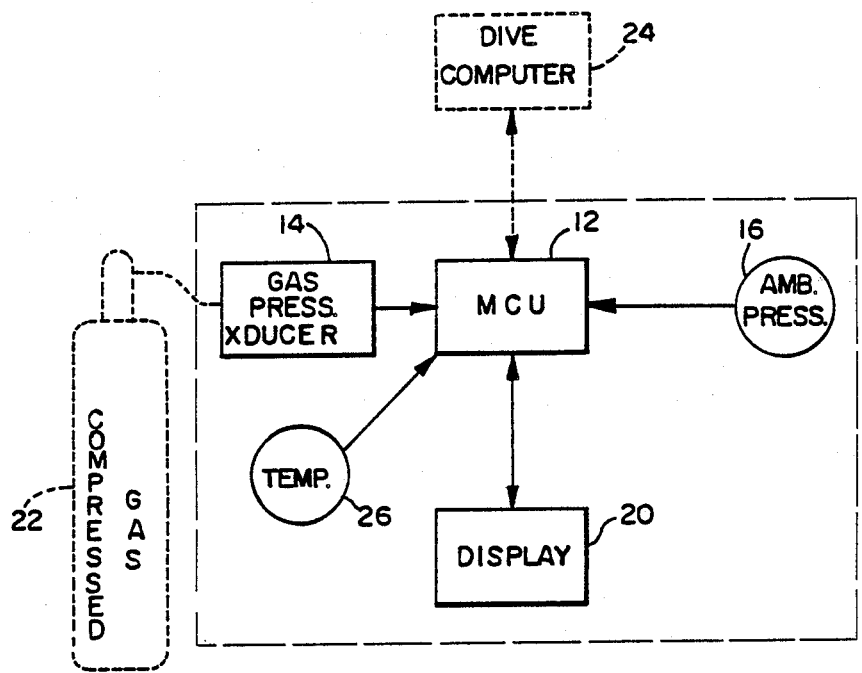
FIG. 1 depicts in block diagram form, the basic components of the preferred apparatus of the present invention.

FIG. 1 depicts diagrammatically the major components of an apparatus of the subject invention. The apparatus includes a microprocessor or MCU 12 or other form of electrical circuit capable of performing the necessary determinations described in detail below, a first pressure transducer 14 which is adapted for coupling with a fixed volume container 22 of breathable gas, a second pressure transducer 16 for sensing ambient pressure to determine the depth of the user of the apparatus and a display system 20 controlled by the microprocessor 12. The first transducer 14 generates a first pressure signal which is sent to the microprocessor from which a consumption rate of the breathable gas in container 22 (indicated in phantom) can be determined. The second transducer 16 generates a second pressure signal which is sent to the microprocessor 12 indicating ambient pressure on the apparatus. A temperature sensor 26 generates a temperature signal which is sent to the microprocessor 12 indicating the temperature in the vicinity of the apparatus. The pressure transducers 14 and 16, the temperature sensor 26 and the microprocessor hardware are all of a type generally well known in the art and commercially available from a variety of known vendors.

Preferably, this basic apparatus is also combined with a conventional diving computer 24 like those described in Jennings U.S. Pat. No. 4,005,282; Villa U.S. Pat. No. 4,192,001; and Seireg et al. U.S. Pat. No. 4,054,783 and in U.S. patent application Ser. No. 787,723, filed Oct. 15, 1985 by Barshinger, all incorporated by reference herein in their entirety. Decompression is discussed in numerous references including Peter B. Bennett, et al., *The Physiology and Medicine of Diving and Compressed Air Work*, Williams & Wilkens Company, 1969, also incorporated by reference herein.

The apparatus of this invention and a diving computer 24 may be combined by the provision of separate elements, as is depicted in FIG. 1 or by the combination of the functions of the subject invention and a conventional diving computer in a single microprocessor (not shown). The diving computer 24 and the associated communication link are indicated in phantom representation to emphasize that a basic form of the invention need not include a diving computer and to further emphasize that even in a preferred form, the invention might employ a single processor performing both functions.

One of ordinary skill in this art will also appreciate that microprocessor 12 would necessarily encompass a CPU or other processing module together with one or more memory modules (RAM, ROM, EPROM, etc.), a clock, a power supply, program or instructions, and other elements and, further, that in addition to an actual display device (or plurality of separate devices) the display system 20 would typically further require some form of memory (e.g. registers, RAM, etc.) and display drivers to store the data being updated by the microprocessor 12 and drivers to drive the display system.

A basic method of operation of the apparatus for SCUBA diving involves determining the remaining gas consumption time that can be expected from the fixed volume container 22.

To determine the consumption rate, it is first necessary to determine consumption rate in terms of pressure drop per unit time. It is possible to use the method of the prior art and, using the signal from transducer 14, simply measure the pressure drop over time and assume that the resulting number is the ongoing consumption rate. There are very large errors inherent in this method in the normal diving situation where the diver is subject to extreme temperature variations. For example, a diver with warm tanks just entering the water might be consuming air at the rate of 20 psi per minute. Three minutes later, when he reaches his destination of 100 feet below the surface, the effect of pressure causes his consumption rate to increase to 80 psi per minute. If during the diver's descent, the temperature drops 17 degrees Celsius, the cooling of the tank air causes a reduction in pressure of almost 10%. If the tank were pressurized to 3000 psi, the pressure drop due to temperature in the first five minutes would be greater than the pressure drop due to breathing. The result would be to double the apparent consumption rate.

It is preferred to monitor temperature and make the necessary corrections mathematically to eliminate the effects on apparent consumption rate of changes in temperature to the breathable gas in the fixed volume container.

The first transducer 14 may be a conventional pressure transducer outputting analog signals indicative of the gas pressure in the container 22. The temperature sensor 26 reads the temperature in the vicinity of the tank 22, which is also the approximate temperature of the gas in the tank, and sends temperature signals to the microprocessor 12. The microprocessor 12 or an equivalent circuit, reads both signals. Using timing from its internal clock, the microprocessor samples the signals at regular, predetermined intervals and determines the change in pressure per unit of time and then uses that information as a base from which to calculate the rate at which the gas is being consumed. Corrections for the effects of temperature on the pressure readings may be made by normalizing either the raw pressure data from sensor 26 or the values calculated from the raw data. Normalization is accomplished by mathematically manipulating all values to remove the effects of temperature variation. For example, the raw pressure readings from transducer 14 can be normalized by the formula:

$$Pn = Pm(Tn/Tm)$$

where all temperatures are in degrees Kelvin or absolute Fahrenheit and Pn is the normalized pressure that would result from changing the temperature from Tm to the normalization absolute temperature Tn, and Pm is the pressure measured at absolute temperature Tm. Pressure consumption rate is then determined by measuring the drop in Pn over a period of time.

Alternatively, it is equally accurate to first determine the uncorrected pressure consumption rate and then correct the result by multiplying it by the ratio of the absolute normalization temperature to the absolute measured temperature.

A more accurate although more complicated method of finding the true pressure consumption rate involves filtering out causes other than breathing that can effect a change in tank air pressure. The more accurate method discards all gradual changes in tank air pressure caused by changing temperature, depth, etc. and all excessive pressure drops caused by free expulsion of gas and looks only at short regular drops in pressure that could be caused by breaths. When a continuing series of roughly equal, short pressure drops is sensed, the more accurate method determines that the events are caused by breathing. It then averages a number of the most recent such events to determine the average breath size and, by measuring the frequency of the events, determines a pressure consumption rate.

In order to separate breath-caused pressure reduction from other causes and to make a reasonably accurate estimate of breath size, it is desirable to measure Tank Pressure (P) with a resolution not presently attainable by purely analog means. With the availability of inexpensive microprocessors and high-resolution analog to digital converters, it is possible to take the output of a pressure transducer, break it into tens of thousands of discrete steps and perform many complex operations on the data developed. To obtain the resolution needed to distinguish breath-caused pressure drops from other causes, it is necessary to have a digitally encoded measurement instrument capable of sufficient resolution so that the change in Tank Pressure (dP) produced from a normal inhale contains at least 10, but preferably more, divisions or measurement units. For a conventional 72 cubic foot SCUBA tank pressurized to 2250 psi, a normal, sea level, 4 liter breath causes a reduction of about 4 psi in tank pressure. For a diver wearing double tanks pressurized to 4500 psi, the same breath would cause a reduction of only 1 psi. To achieve the minimum necessary resolution of at least 10 counts per breath, the measurement instrument would have to measure accurately a dP of less than 0.1 psi.

The accurate method of determining pressure consumption rate is best understood if tank pressure is thought of as being measured in steps or counts equivalent to the minimum resolution. For a single tank pressurized to 2250 psi, full pressure would be represented by at least about 22500 counts to give a resolution of 0.1 psi per count. To make the apparatus versatile enough to be usable on a 4000 psi SCUBA tank, the minimum number of counts required is about 40,000, and, more desirably, allowance for 80,000 counts should be provided, each count representing 0.05 psi, an empty tank having 0 counts.

Figure 7:
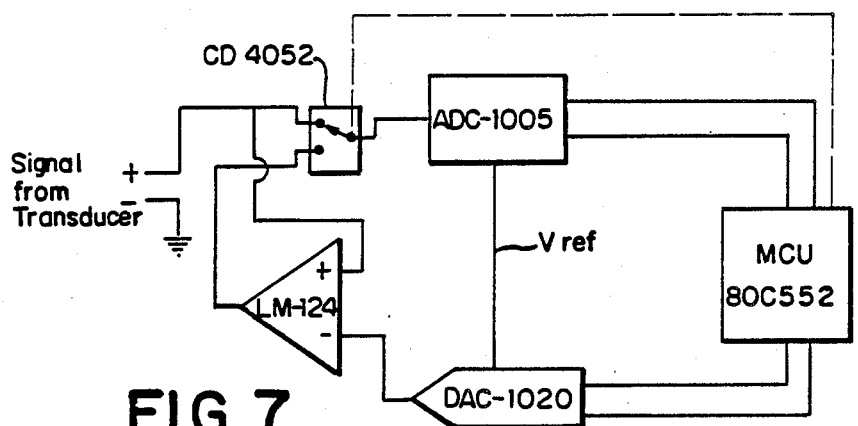
FIG. 7 depicts diagrammatically a circuit providing high digital resolution of an analog pressure signal.

At the present time, most of the Analog to Digital converters available with 80,000 counts of resolution or more tend to be both slow and expensive. These problems can be surmounted by other methods that are somewhat more complicated, but offer the potential of being faster, more accurate and somewhat less expensive. For example, the resolution and accuracy of the Analog to Digital conversion can be enhanced by comparing the analog output of the transducer with its digital interpretation, and then "zooming in" on any difference for a higher resolution reading. FIG. 7 shows a simplified schematic diagram of such a circuit. In FIG. 7, the analog signal from the transducer 14 is digitized by the analog to digital converter, ADC 1005, (set to always round down) and, via the microprocessor, 80C552, fed to the digital to analog converter, DAC 1020, where it is converted back to an analog signal. This "reconstituted" analog signal is then compared to the original signal in the LM-124 differential amplifier, any difference amplified by a factor of 256, and fed back into the ADC through the analog switch, CD-4052, switched to "B" position for digitizing. The effect of this process is to act as a vernier. The first digitized reading establishes the closest major division, the second reading establishes the closest minor division. If the ADC and DAC are 8 bit devices (256 counts), then the major divisions for a 5120 psi capability are 5120 psi/256 or 20 psi per count. The minor divisions are then 20 psi/256 or 0.078 psi. This resolution can be improved even further by using 10 bit DAC and ADC chips and setting the gain of the differential amplifier to 1024. Using such a 10 bit arrangement, resolution becomes better than 0.005 psi, meaning the system can sense a dP of less than 0.005 psi. The microprocessor shown in this example can be either dedicated to the pressure circuit or it can be the same microprocessor being used by an associated dive computer 24 (FIG. 1).

Figure 6:
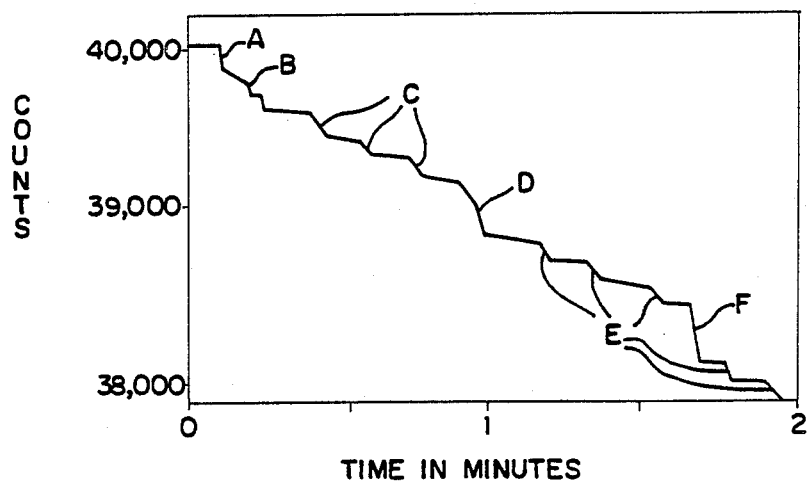
FIG. 6 depicts a pressure signal generated from a fixed supply of bottled gas during use by a diver.

FIG. 6 charts an example graph of SCUBA tank pressure measured in counts vs. time for the first few minutes of a typical dive. The sharp or more steeply sloped drops produced at points "A" and "B" in FIG. 6 are due to the diver clearing his regulator and breath testing his system. The gradual down-sloping of the line after point "B" is due to dropping temperature in the air tank as the diver enters cool water. The small drops "C" and "E" are caused by normal breathing. The somewhat larger drop "D" is due to the diver taking a single deep breath. The large, steep drop at "F" is due to the diver using his air supply to inflate a lift bag.

Pressure consumption rate due to breathing is preferably computed by first finding an average breath (pressure drops "C" and "E" in FIG. 1). An average breath will produce a pressure drop in relation to the size of the tank. So that the apparatus can be adaptable to many different tank sizes, it is preferred that the pressure drop produced by an average breath be empirically determined.

It is first necessary that the pressure signals from the transducer be analyzed and characterized as a series of individual pressure drop events. This can be done by finding the average pressure change over a sample period of time such as, for example, two (2) minutes, and selecting for study only those events where the event pressure drop rate exceeds the average period pressure drop rate. To improve the probability that selected events will be breaths, the definition of an event may also require that the event pressure drop rate have a minimum duration of, for example, 0.5 seconds, a maximum duration of, for example, 4 seconds, and a minimum space of, for example, 1 second between events. Short pressure drops spaced closer than the minimum space would be considered a single event. Each selected event is then compared by size (total event pressure drop) with all the other events selected in the sample period. If within the sample period, some significant percent, such as about at least 70% of the selected events are found to have a pressure drop within an acceptable range, such as within about 50% of each other, the apparatus identifies these "qualifying" events as breathing events.

A similar and even more effective means of finding qualifying, breathing events involves the steps of: (1) measuring and tracking the average rate of pressure change over a period of time such as, for example, a minute or two; (2) selecting as events those periods of qualifying duration and spacing where the pressure drop rate exceeds the average; (3) identifying as qualifying events those selected events representing pressure drops that fall within 50% of each other when at least a majority out of any string or series of 20 selected events so qualify.

Once the average qualifying breathing event has been found by either of these methods or any other method, any subsequent event is considered to qualify as a breathing event so long as it falls within a suitable range such as, for example, +100% and −50% of the average pressure drop per event. For the purposes of determining gas consumption rate, a running average of a number such as, for example, the last 10 to 20 qualifying events, is maintained, and the average breath pressure drop is recalculated after each breath. For other uses, it may be desirable to use weighted or other forms of averaging.

The process of determining a qualifying event may be made even more accurate by incorporating information about ambient pressure. As a SCUBA diver descends deeper, ambient pressure will increase and each breath will cause a correspondingly greater drop in pressure. Ambient pressure may therefore be used to modify the event qualification window to more accurately bracket the expected breath pressure drop when ambient pressure changes. For example, if the diver had spent several minutes at 16 feet, with an average pressure drop of 3 psi per breath, the Event Window would stabilize at 1.5 to 6 psi (3 psi−50%, +100%). Were the diver to descend to 99 feet, his average breath would cause a pressure drop of 8 psi, the pressure drop being directly proportional to the absolute pressure. If the descent happened quickly, then the diver might come close to overrunning the upper limit of his Event Window. Modifying the Event Window according to ambient pressure improves the accuracy of qualification. In the case of the foregoing example, ambient modification would have moved the Event Window from the range 1.5-6 psi to the range 4-16 psi as the diver reached 99 feet.

Once the breathing (qualifying) events have been identified, an average rate of gas consumption, in terms of pressure drop, is determined by multiplying the average pressure drop of the qualifying events by the frequency of occurrence.

The methods for determining breathing consumption illustrated above all use pressure drop data as a starting point. It is equally possible to use other indicia of consumption such as, for example, flow rate data. A simple method of measuring flow rate is to measure the pressure drop across an impedance at some point in the circuit supplying gas to the user. In such a system, consumption calculations are made easier because pressure drop across the impedance is approximately directly proportional to the rate of gas consumption. Breathing from such a system will produce a series of signals which, by their amplitude and duration, will give a direct indication of the amount of gas consumed by each event. Filtering out non-breathing events and finding the consumption and frequency of average breathing events can be accomplished in the same manner as described herein for pressure drop events. To be useful, consumption data determined in this way must be converted to data that represents consumption as a percentage of the total gas volume available. Conversion can be accomplished by either comparing the consumption rate to the known volume of gas available or by measuring the correlation between a measured consumption and a measured pressure drop of the gas in the fixed volume container. In either case, volumetric consumption data is converted to data representing the rate at which the breathable gas is being expended in comparison to the total amount of breathable gas remaining.

Regardless of the means used, once a consumption rate (dP/dT) has been determined, a consumption time value for the breathable gas remaining in the fixed volume container 22 and remaining air time values for various depths can be determined.

By dividing the current tank pressure P by the current consumption rate, the Remaining Air Time (RAT) is obtained. RAT is a value that represents the amount of time it would take to consume the remaining gas in container 22 if the present consumption rate were maintained. The RAT value is regularly updated by the microprocessor 12 to reflect changes in the rate of consumption during the dive.

A SCUBA diver, however, needs more than the RAT. A diver does not normally stay at a single depth. If the RAT was calculated from breathing near the surface, his air time at deeper depths will be substantially less.

Conversely, at the end of his dive, the diver will ascend to the surface. A RAT calculated from a consumption rate measured at depth will not reflect the substantial increase in usable air time gained from the ambient pressure reduction that occurs during ascent. The increase in Remaining Air Time upon ascending is very important, especially when it is necessary for a diver to decompress for a period of time at shallow depths before surfacing. It would be very useful therefore if the Remaining Air Time could be presented to a diver in a manner that indicates immediately the Remaining Air Time at various depths so that the diver will have an immediate and better understanding of how long his remaining air supply will last were he to rise, or descend further, during his dive.

Accordingly, an important aspect of the present invention is that the apparatus can further determine at least one other Remaining Air Time value at a depth (ambient pressure) different from the existing depth. This allows the user to see his Adjusted Remaining Air Time (ARAT)—the amount of time that his supply of gas from tank 22 will last if he changes depth (ambient pressure). Preferably, the apparatus calculates a multiplicity of ARAT Times at a multiplicity of depths both above and below the current depth of the user.

Adjusted Remaining Air Time Times can be determined from the following formula:

$$ARAT_{Pn} = RAT_{Pk}(Pk/Pn)$$

where $ARAT_{Pn}$ is the Adjusted Remaining Air Time time at any absolute pressure Pn and $RAT_{Pn}$ is the RAT at any absolute pressure Pn. In terms of depth below the surface of the ocean, $$ARAT_{Dn} = RAT_{Dk}(Dk+33)/(Dn+33) \quad (1)$$

where $ARAT_{Dn}$ is the Adjusted Remaining Air at any depth Dn expressed in feet below the surface of sea water, $RAT_{Dk}$ is the Remaining Air Time at some known depth Dk. The constant 33 is used if the depth calculations are in feet of sea water. If the calculations are to be in meters of sea water, the constant becomes 10. If the calculations are to use fresh water instead of sea water, the appropriate constant should be multiplied by 0.975 (33 becomes 32 for English measurements and 10 becomes 9.8 for metric).

Although knowing the Adjusted Remaining Air Time is useful and a significant improvement over the present state of the art, it is even more useful to also take into account the air required for the diver's ascent to the surface. The Safe Air Limit (SAL) time as herein defined is the predicted maximum amount of time that a diver may stay at a particular depth and still have enough air to complete an optimum ascent to the surface (Safe Ascent Profile) from that depth, including any allowance for decompression stops and reserve.

To find the Safe Air Limit, it is first necessary to determine the Ascent Air Requirement—the amount of gas that would be consumed by ascending to the surface from a particular depth by following the Safe Ascent Profile.

The Safe Ascent Profile information is best provided by a dive computer 24 that has been tracking the absorbed gasses in the diver's tissues and can provide projections of depth and time values that the diver should follow to make a safe ascent not only if the ascent begins immediately, but also if the ascent begins at some time in the future. This profile information must stipulate how much time the diver must spend at each depth on his way to the surface. For ease of calculation, the ascent can be divided into 10 foot increments, and a dwell time determined for each increment. Knowing already the pressure consumption rate (dP/dT) at the diver's present depth, it is a simple matter to determine what the pressure consumption rate will be in each increment (consumption rate being directly proportional to the absolute pressure) and multiply that rate by the increment's dwell time to find the pressure consumption in each increment. The total of all incremental consumptions will be the required amount of air pressure needed to make the safe ascent, i.e. the Ascent Air Requirement (AAR). The Ascent Air Requirement value may be presented to the diver as a pressure value. For example, the diver may be advised that he will require 550 psi of air to surface and/or decompress. By comparing the Ascent Air Requirement pressure with the present air supply pressure, the diver can estimate how soon he should begin his ascent. In the preferred form, this comparison is made by the microprocessor and presented to the diver as a time value representing the safe limits of the remaining air supply—the Safe Air Limit. So long as the diver ascends within his No-decompression Time limit, the Safe Air Limit can be simply determined by subtracting the AAR value from the remaining air supply value (P) and then dividing the difference by the present gas consumption rate (dP/dt) according to the formula:

$$SAL_{Dl} = (P - AAR_{Dl})/(dP/dt_{Dl})$$

where $SAL_{Dl}$ is the SAL at depth Dl, $AAR_{Dl}$ is the AAR from depth Dl, and $dP/dt_{Dl}$ is the present consumption rate adjusted for Dl.

Figure 2:
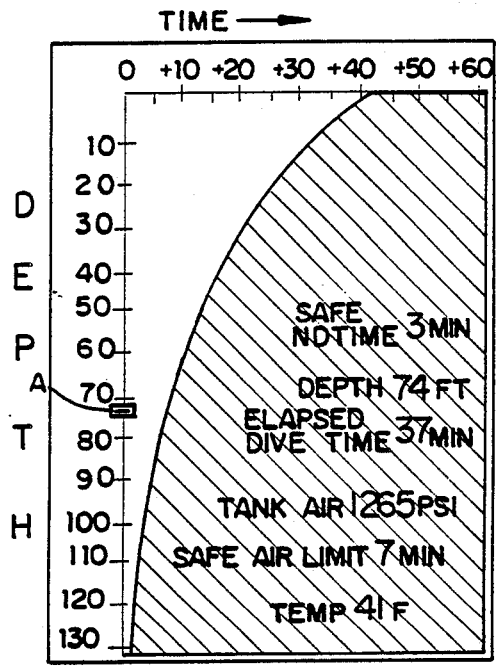
FIGS. 2 through 5 depict various displays of remaining breathable air in terms of time and depth.
Figure 3:
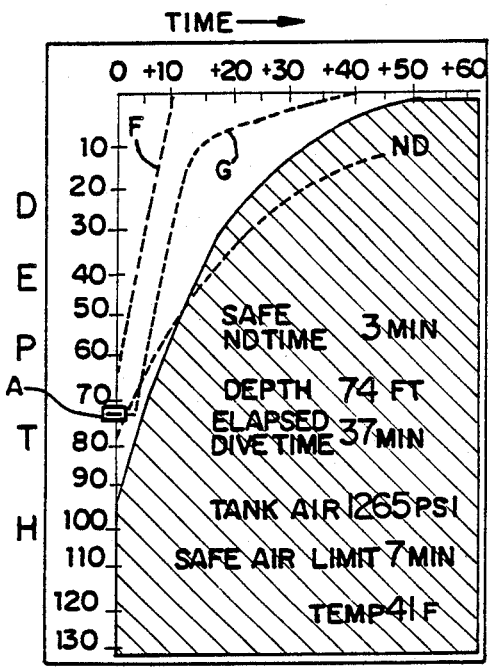

However, if the diver is to have the option of making a delay for decompression during his ascent, the Ascent Air Requirement calculation requires an extra series of steps. Because of the physiology of decompression, the required decompression delays are lengthened disproportionally with additional time at depth. Five extra minutes at depth may lengthen the decompression time by 20 minutes. As a result, in order to determine how much longer a diver may stay at depth and still have enough air to decompress safely, it is necessary to make projections of future ascent profiles. These pro-forma ascent projections can be easily supplied by the dive computer simply by adding hypothetical time to the diver's present depth as far into the future as needed to find the point at which there will be just sufficient air to make a safe ascent. In other words, the dive computer assumes that the diver stays longer and longer at this present depth until just before the present consumption rate plus the Ascent Air Requirement exceeds the amount of air available, less any allowance for reserve. This point in the future represents the Safe Air Limit time. For the calculations that follow, it is useful to first find the Total Air Required (TAR) for an additional time at some depth and then a safe ascent to the surface.

$$TAR_{Dlt1} = t1(dP/dt_{Dl}) + AAR_{Dlt1}$$

where t1 is additional time at the present depth; $TAR_{Dlt1}$ is the Total Air Required to stay at depth Dl for the additional time t1 and then ascend; $AAR_{Dlt1}$ is the AAR calculated for an ascent beginning in the future from depth dl at time "now plus tl." $dP/dt_{Dl}$ is the present consumption rate adjusted to depth Dl. As an example, consider a diver at 120 feet depth, consuming 90 psi per minute, and who is just about to enter the decompression-required zone. If he were to ascend now, his ascent could be direct, would take only 3 minutes, and would use a calculated 140 psi. If he were to stay 5 minutes longer, his ascent would require a 10 minute decompression stop and therefore use a calculated 400 psi. Thus, to stay another 5 minutes, the diver would need 850 psi (TAR5=90 psi/min×5 min plus 400 psi to ascend). If the diver's tank reads only 860 psi above his reserve, the display would tell the diver that this air supply will allow him to stay only another 5 minutes. In FIGS. 2 and 3 this information is displayed as "Safe Air Limit 7 min." It could also be added to the displays of FIGS. 4 and 5 and any other display, if desired.

Figure 5:
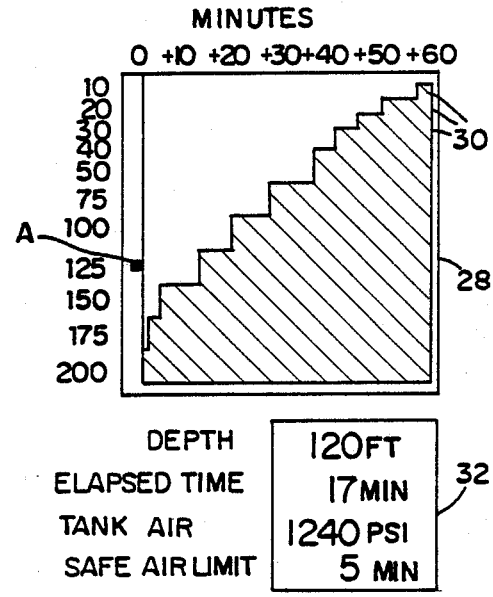

In its simplest form, the display 20 includes means for displaying numerically the calculation results. In the preferred form, the display 20 also presents a Pictorial representation of the above-described calculation results. FIG. 5 depicts diagrammatically an example of a simple Pictorial Display that might be generated using a liquid crystal display device 28 to depict Safe Air Limit time values as a series of bars 30 corresponding to depth. The bars 30 appear to move across the display 28 from right to left as air is consumed. In this figure, the top four bars represent Safe Air Limit times at 10, 20, 30 and 40 foot depths, while the remaining seven bars indicate Safe Air Limit times, for example, at floor depths of 50, 75, 100, 125, 150, 175 and 200 feet. The diver's approximate depth and relationship to the Safe Air Limit times can also be visually indicated, such as, for example, by darkening the appropriate bar in a vertical row along the left edge of the display next to a depth scale. In addition to the bars 30, the LCD may also include a numerical section 32 presenting more precise tank air pressure, depth and time information as read by the two transducers and calculated by the microprocessor 12. Other information such as elapsed time can easily be determined by the microprocessor 12 using its internal clock.

FIG. 2 shows an exemplary Pictorial image generated on the screen of a high density LCD display device wherein depth is shown on the left vertical axis, time on the upper horizontal axis, and the diver represented by the symbol denoted "A" on the left vertical axis depth scale. The curved line separating light and dark areas is the Adjusted Remaining Air Time (ARAT) line and represents to the diver that point in time at the various displayed depths when his air supply will be exhausted (except for safety reserve). Displayed in this manner, the diver can see in a quick and easily comprehended manner how much air safety he has remaining. So long as he stays in the white area of the display he has air, in the black area of the display he has none. As the diver continues to use air, the (ARAT) line will slowly move towards the diver depicted at the zero time line (i.e. towards the depth axis along the left side of the display) while at the same time becoming more parallel to the zero time line (i.e. vertical in the depicted display) At the time at which the air is exhausted, (ARAT) line will be a straight vertical line overlapping the depth axis, indicating that there is insufficient air remaining at any depth. In FIG. 2 the diver is given his ARAT in Pictorial form and his SAL in numerical form. It is quite possible to additionally or alternatively supply the SAL in Pictorial form.

In the preferred form of presentation, the LCD display device has sufficient resolution to generate each alphanumeric character with a 3×5 and, preferably, a 5×7 dot matrix. When the diver first enters the water, his position is represented by the symbol, indicated by "A" in the figure, in the upper left portion of the screen, on the surface. As he descends, his "image" descends on the screen. Preferably, when his "image" reaches a point about two thirds of the way down it goes no lower, but the depth scale begins to scroll upwards. This ensures that no matter how deep the diver goes, there is always visible to him an indication of what happens to his air supply if he goes deeper. On the LCD display depicted in FIG. 2, the horizontal scale at the top of the display represents future time (now+10 minutes, now+20 minutes, etc.). The diver's position at the left side along the depth scale represents the present moment (i.e. 0 future time). Events off to the right of the diver represent the future and move slowly from right to left towards the diver's position. The effectiveness of this form of presentation is that the diver sees ahead of him his position in a Safe Operating Envelope, and can see Pictorially both his options and what he must do to avoid running out of air.

With computations provided by a dive computer, it is possible to add a graphic representation of a Safe Ascent Profile for both the present moment and at times in the future. FIG. 3 shows such a display where the line "F" represents the present Safe Ascent Profile, i.e. the profile the diver would take should he decide to surface immediately. Using the same equations, it would be possible to determine and display a Safe Ascent Profile for a future time by projecting ahead a profile for the diver remaining at depth for some selected time. Line "G" shows what the safe ascent profile will be if the diver stays at his present depth another 7 minutes. In this case, the profile shown by "G" assumes that the diver will have stayed beyond his safe no-decompression time and will be required to make a slower decompression ascent. As can be seen, the ascent profile "G" remains clear of the Safe Air Limit Line during the decompression period. The diver therefore knows that he can stay no more than seven minutes longer at his present depth without the risk of running out of air during decompression. The computer can be programmed to calculate and display a future time profile line for a fixed predetermined future time or to calculate a series of profiles, compare them with the Adjusted Remaining Air Time (ARAT) line and display the last profile calculated not to intersect a future Adjusted Remaining Air Time (ARAT) line. Various alarms or other warnings can be incorporated to signal the diver when he must begin his ascent to avoid running out of air.

Preferably, the Pictorial Display format is also used to present other information from a dive computer 24 that will further enhance the diver's intuitive comprehension of his situation. It is particularly desirable to Pictorially display critical safety information to the diver in a manner that provides the diver with a visual reference for his position in comparison with his Safe Operating Envelope. In FIG. 3, line "ND" is a No-decompression line and represents the length of time a diver may stay at any of the indicated depths without being required to decompress. An initial ND line can be obtained or determined from publicly available information such as U.S. Navy Dive Tables and stored in memory of the microprocessor 12. Preferably, the position of the ND line is determined in real time by or in conjunction with the dive computer 24 by taking into account the degree of nitrogen saturation calculated to be present in the diver's tissues based on the diver's prior activities. With the inclusion of the ND line, the diver can clearly see the point at which any further delay at depth will require decompression with a corresponding increase in air required to get to the surface. Like the ARAT, the ND line generated in either way will slowly move towards the diver (i.e. left edge of figure), reaching the diver when he enters the "decompression required" zone.

Figure 4:
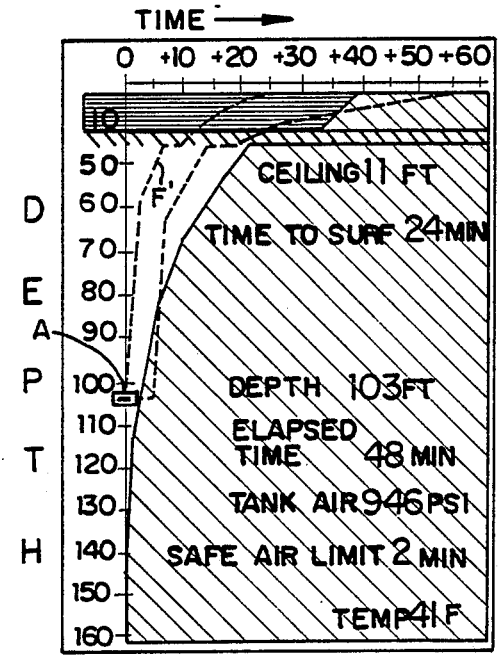

When the diver crosses the ND line and decompression is required, he is no longer permitted to ascend directly to the surface but must pause at a decompression stop or Ceiling. The depth of the Ceiling is calculated by or in conjunction with the dive computer and is continuously updated. When the diver crosses the ND line, the ND line no longer has any meaning. If at that point, the ND line is replaced by a Ceiling representation, then the diver is presented with every piece of information he needs to conduct a safe dive—his Safe Operating Envelope. FIG. 4 shows a suggested display, based upon the display of FIG. 3, for use after the diver has crossed the ND line. The ND line of FIG. 3 has been replaced in the display of FIG. 4 with a ceiling representation shown in the figure by a series of short diagonal lines extending across the display at the ceiling depth (11 feet in this example). A new present safe ascent profile F' has been determined and displayed indicating the required decompression stop. The diver's Safe Operating Envelope is plainly seen, bounded by the Ceiling representation, the depth scale (representing the present time) and the Adjusted Remaining Air Time line, and the diver can easily tell where he is in relation to the limits of his safety. As seen in FIGS. 2 through 5, other various useful numbers can be presented in numerical form in the display.

Figure 8:
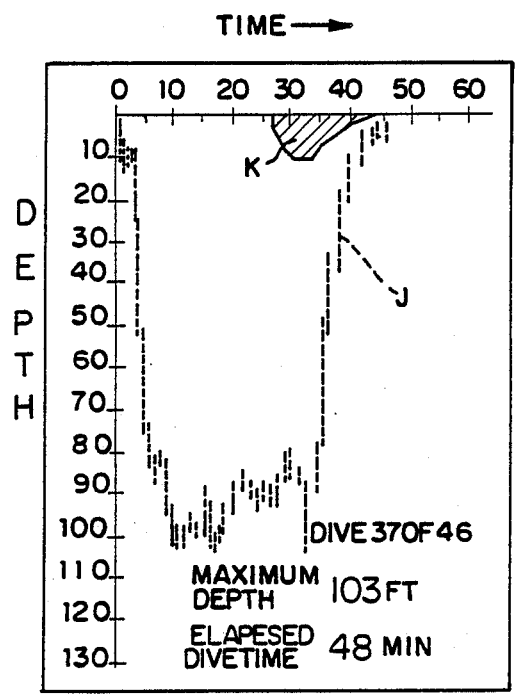
FIG. 8 depicts diagrammatically a history of a diver's depth and time for a completed dive.

Once the diver's instrument contains a Pictorial Display, it is possible to present some very useful information to the diver when he reaches the surface. In the Pictorial screen of FIG. 8, line "J" presents a history of the diver's depth and time on a previous dive. The area "K" of FIG. 8, represents Pictorially the time of occurrence when a Ceiling had been present during the dive and the various depths of that Ceiling at the times indicated along the top margin. This information allows the diver to plan future dives, particularly dives occurring within the next twenty-four hours, which may be affected by nitrogen remaining in the diver's slow tissues. In addition, the information permits the diver and/or his instructor to analyze the prior dive and to see the exact activity profile.

To avoid unnecessary complication, many possible refinements have been left out of the preceding discussion. For example, it is considered good practice to always keep a small reserve in the air supply. Therefore in a practical implementation of this invention, safe time numbers and displays would allow for a reserve. Similarly, this invention and an associated dive computer are discussed as two separate instruments. In practice, both instruments may be in the same case or even use the same microprocessor. Also, the Remaining Air Time, average consumption rate, Safe Air Limit, Adjusted Remaining Air Time, and the other parameters are calculated continuously and the displays continuously updated. Various well known algorithms may be used to improve processing speed and reduce the amount of processing time needed to make the necessary calculations. For example, in making the first trial calculation for the Safe Air Limit (SAL), the computer may select a time 99 minutes in the future and make a Total Air Required (TAR) projection for that time. If there is sufficient supply air to make the surface more than 99 minutes from the present (which will usually be the case when the diver is just beginning his descent), the SAL may be shown as "greater than 99 minutes." In such case, the computer would continue to make TAR calculations only for "now plus 99 minutes" until the TAR reached the remaining air supply level. Various well known bracketing techniques will aid the computer's task in finding and keeping just the right SAL time.

Similarly, the time period used to find the average consumption rate might be relatively long when the instrument is first turned on to be sure of getting an established and reliable breathing pattern. Once a good pattern is established, the time-averaging period can be shortened to make the instrument more responsive to changes in the diver's activity level. It is also possible to allow the diver to choose that the computations for air used during decompression use a standard "at rest" breathing rate rather than be influenced by the diver's breathing rate while working hard at some task just before ascending.

In the implementations described herein, pressure and pressure drop have been used as the primary indicia of gas consumption. There are other methods of determining gas consumption rate which would provide the raw information needed for certain aspects of the present invention.

The displays of FIGS. 2, 3, 4, and 5 show the diver's position as fixed on the left margin. Other effective display formats could show the diver on another margin or could track his course across the screen in a manner similar to the depth-time line of FIG. 8.

The figures presented here are drawn to illustrate concepts only. They are not intended to reflect the actual limits that a user would encounter during a dive.

It will be recognized by those skilled in the art that changes could be made to the above-described preferred and other embodiments of the invention without departing from the broad, inventive concepts thereof. It is understood, therefore, that this invention is not limited to the particular embodiments, arrangement or steps disclosed, but it is intended to cover any modifications which are within the scope and spirit of the invention, as defined by the appended claims.

I claim:

1. A portable diving apparatus with a means for displaying to a diver critical safety information relating to depths and times, the information being displayed in a two dimensional Pictorial format and in a manner that provides the diver with a visual reference for his condition at the current depth in comparison with potential conditions at other times and depths where the diver may operate safely.

2. The apparatus of claim 1 wherein the display means is a two dimensional Pictorial Display including a graphic presentation of the position of the diver in depth and time and in relation to the various bounds of the Safe Operating Envelope and containing at least one of the following elements:
   a display format wherein the bounds of the Safe Operating Envelope are presented by lines; and
   a high density dot matrix display device wherein displayed information is formed by exciting certain dots in the dot matrix.

3. The apparatus of claim 2 wherein the bounds of the Safe Operating Envelope are defined by at least two of the following elements:
   a representation of the Adjusted Remaining Air Time at various depths;
   a representation of the Safe Air Limit at various depths;
   a representation of the No-decompression Times at various depths;
   a representation of the Ceiling; and
   a representation of the water surface.

* * * * *